United States Patent [19]

Mohrman et al.

[11] 4,093,360
[45] June 6, 1978

[54] OPHTHALMIC INSTRUMENT OPTICAL SYSTEM

[75] Inventors: Richard C. Mohrman; Richard L. Seidenberg, both of Rochester, N.Y.

[73] Assignee: Bausch & Lomb Incorporated, Rochester, N.Y.

[21] Appl. No.: 722,952

[22] Filed: Sep. 13, 1976

[51] Int. Cl.[2] ............................................. A61B 3/10
[52] U.S. Cl. ........................................ 351/13; 351/6
[58] Field of Search .......................... 351/6, 9, 13, 16

[56] References Cited

U.S. PATENT DOCUMENTS

| | | | |
|---|---|---|---|
| 2,388,858 | 10/1945 | MacNeille | 351/9 |
| 3,664,730 | 5/1972 | Cardona | 351/6 |
| 3,791,720 | 2/1974 | Walker | 351/9 X |

*Primary Examiner*—Paul A. Sacher
*Assistant Examiner*—Rodney Bovernick
*Attorney, Agent, or Firm*—Frank C. Parker; Bernard D. Bogdon; Robert S. Beiser

[57] ABSTRACT

An ophthalmic instrument is constructed with an aligning axis for aligning the instrument to the cornea of an eye and first and second operating modes. The first operating mode measures the corneal curvatures in two orthogonal planes and the second operating mode examines at least the surface of the cornea. The instrument has an eyepiece, an imaging system, and a reflecting system. The eyepiece is disposed on the aligning axis. The imaging system has an axis that is displaced from and substantially parallel to the aligning axis and is used in the first and second modes. The reflecting system displaces an image from the aligning axis to the optical axis and provides an erect image of the displaced image at the eyepiece in the second mode.

3 Claims, 3 Drawing Figures

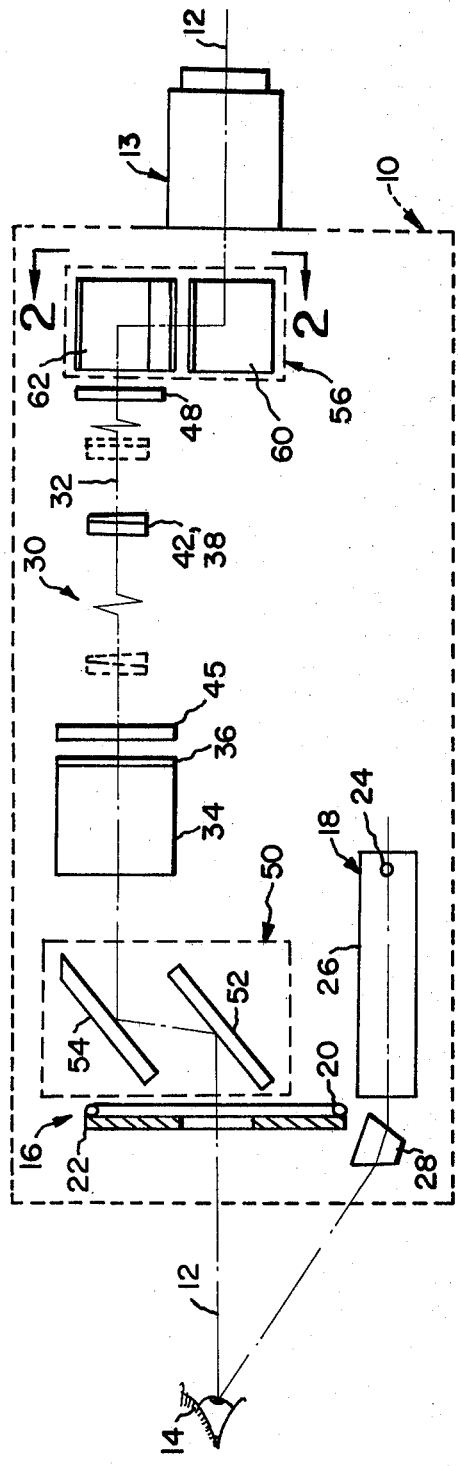
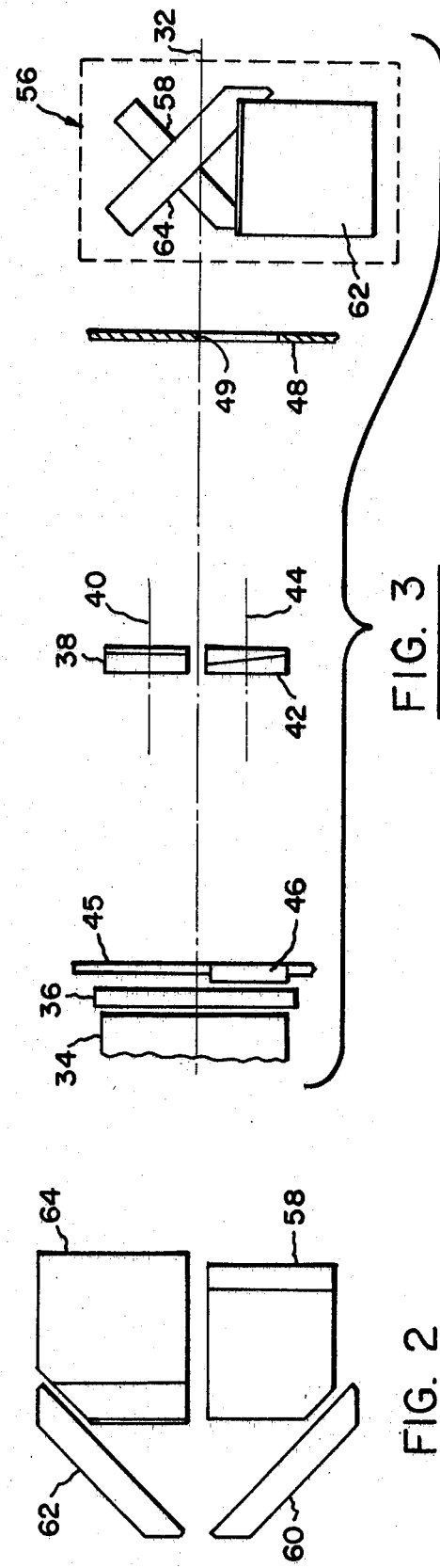

OPHTHALMIC INSTRUMENT OPTICAL SYSTEM

BACKGROUND AND SUMMARY OF THE INVENTION

For many years optometrists, ophthalmologists and individuals engaged in eye research have used instruments for studying the eye. Some of these instruments have been used to merely view parts of the eye with or without a contact lens placed thereon; such as, magnifying glasses, slit-lamps and biomicroscopes. Other instruments, commonly called keratometers or ophthalmometers have been used to measure the corneal curvature along the two principal meridians of the eye. The principles of operation of such instruments are well known in the prior art, as shown in U.S. Pat No. 3,791,720 of Walker et al, and the chapter "The Keratometer" published in *Clinical Ophthamology*, 1976 by applicant Mohrman.

A relatively recent development in ophthalmic instruments has been the development of an instrument that will not only measure the corneal curvatures along the two principal meridians of the eye, but also permits examination of the surface of the cornea with or without a contact lens fitted thereon and the anterior chamber of the eye. One of these instruments merely uses an insertable mask to eliminate the images from all, but one light path. Some disadvantages to this instrument, however, are excessive vignetting and image doubling under certain conditions and an inverted image of the cornea in the viewing mode. Another such instrument embodies two distinct optical systems for the two modes of operation. One optical system provides the measurement of the corneal curvatures along the two principal meridians of the eye and the second optical system provides a magnified image of the surface of the cornea. The mode of operation of the instrument is determined by moving a lever connected to a mask and reflector. In the measuring mode, the image passes through an objective lens, a mask, adjustable optical wedges and through an eyepiece to the user's eye. In the viewing mode, the image is reflected from the optical axis of the measuring system to the optical axis of the viewing system. As light reflected from the cornea progresses through the viewing system, the image is magnified while bypassing the measuring system and returned to the eyepiece of the ophthalmic instrument for viewing. A major disadvantage of this instrument is the expense due to the cost of manufacturing separate optical systems.

In the present invention, an ophthalmic instrument is provided that has an aligning axis for aligning the instrument to the eye and is operable in first and second operating modes. The first operating mode is used to measure the corneal curvature along the two principal meridians of the eye and the second operating mode is used to examine at least the surface of the cornea. In the second operating mode, the surface of the cornea with or without a contact lens fitted thereon and the anterior chamber of the eye may be examined. The instrument includes an eyepiece, an imaging system and reflecting apparatus. The eyepiece is disposed on the aligning axis. The imaging system has an axis displaced from and substantially parallel to the aligning axis and measures the cornea in the first mode and examines the corneal surface in the second mode. The reflecting apparatus displaces an image from the imaging axis to the optical system axis and provides an erect image of the displaced image at the eyepiece in the second mode.

BRIEF DESCRIPTION OF THE DRAWINGS

Objects and advantages of the invention will become apparent upon reading the following description and upon reference to the drawings, in which like reference numerals refer to like elements in their various views:

FIG. 1 is an elevational view, partly in section, of an embodiment of the present invention.

FIG. 2 is an elevational view taken along lines 2—2 of the invention illustrated in FIG. 1.

FIG. 3 is an enlarged plan view, partly in section, of a portion of the invention illustrated in FIG. 1.

DETAILED DESCRIPTION OF THE PREFERRED EMBODIMENT

As best seen in FIG. 1, an ophthalmic instrument 10 is constructed with an aligning axis 12 and an eyepiece 13 disposed on axis 12. Aligning axis 12 is used to align the instrument 10 substantially coaxially with the optical axis of an eye 14. Preferably, aligning axis 12 is also an axis of rotation when ophthalmic instrument 10 is used in the measuring mode.

To provide the necessary illumination in the first and second modes, a measuring light apparatus 16 and a viewing light apparatus 18 are provided. Measuring light apparatus uses a fluorescent light 20 and mire 22. Mire 22 may be described as an opaque member having a circular aperture through its center, and circulinear aperture around this center aperture. A pair of cross mark like apertures are disposed along the horizontal axis of the circulinear aperture and a pair of dash mark like apertures are disposed on the vertical axis of the circulinear aperture. When light 20 is activated, the light passing through these apertures strikes the patient's cornea and produces an image behind it which is reflected from eye 14. This reflected light is the image passing through instrument 10 in the measuring mode. Viewing light apparatus 18 has an incandescent lamp 24 disposed within an enclosure 26 and a refracting member 28. When lamp 24 is activated, the light reflected from eye 14 passes through instrument 10 in the viewing mode.

As best seen in FIGS. 1 and 3, an imaging system 30 is disposed along an axis 32 within instrument 10. System 30 uses an objective lens 34, a mask 36, a first optical wedge 38 with a first optical axis 40 and a second optical wedge 42 with a second optical axis 44. Objective lens 34 takes the image of the mire reflected from the eye, divides it into four light paths and focuses it through mask 36. Mask 36 is an opaque screen having four apertures therethrough at right angles to each other. Light passes through the top and bottom apertures and focuses on reflecting system 56 to form a first image of mire 22. Light passing through the horizontal apertures passes through first optical wedge 38, and second optical wedge 42, respectively. These wedges form a second image of mire 22 above the previously mentioned first image, and a third horizontal image beside the first image. The cross marks and dashes of the 3 mire images are then aligned by moving wedges 38 and 42. The movements are measured, and the measurements indicate the curvature of the cornea because the misalignment of the three mire images is in proportion to the distortion of the original mire image as it passed through the curvature of the cornea. These individual elements are well known in the art and are used in a conventional manner. Imaging system axis 32 is, however, displaced from and substantially parallel to axis 12. Preferably, system axis 32, first optical axis 40 and second optical axis 44 lie in a plane that is disposed tangentially to a cylinder whose center is aligning axis 12.

To provide a viewing mode for instrument 10, an insertable mask 45 carrying third optical wedge 46 and an insertable mask 48 having aperture 49 therethrough are included within optical system 30. Mask 45, wedge 46 and mask 48 are inserted into optical system 30 when instrument 10 is used in the viewing mode and withdrawn from system 30 when instrument 10 is used in the measuring mode by mechanical apparatus (not shown). Wedge 46 is used in conjunction with optical wedge 42 for shifting the image passing through wedge 46 and wedge 42 from the second optical axis 44 toward the system axis 32. Insertable masks 45 and 48 are used to prevent passage of light along any optical axis other than light passing along second optical axis 44. Mask 45 is a movable opaque screen. Mask 48 is an opaque screen having an aperture 49 through its center.

Reflecting systems 50 and 56 displace an image passing through instrument 10 to imaging system axis 32 and provides an erect image of the displaced image at eyepiece 13. A first reflecting system 50 displaces the image from aligning axis 12 to system axis 32 by using two front reflecting plano mirrors 52 and 54. A second reflecting system 56 returns the image from system axis 32 to aligning axis 12, while erecting the image of the cornea in the viewing mode. This result is accomplished by using four front reflecting plano mirrors 58, 60, 62 and 64.

In operation, aligning axis 12 of instrument 10 is substantially aligned with the optical axis of eye 14. When instrument 10 is used in the first operating mode, insertable optical wedge 46 and insertable masks 45 and 48 are withdrawn from imaging system 30 and lamp 20 is activated. An image of the apertures of mire 22 reflected from eye 14 are reflected from aligning axis 12 to system axis 32 by first reflecting system 50, through objective lens 34, mask 36, optical wedges 38 and 42, reflected from axis 32 to aligning axis 12 by second reflecting system 56 and through eyepiece 13 to the eye of the user. As previously mentioned three separate images of mire 22 are thereby formed at right angles to each other. Instrument 10 is then rotated about aligning axis 12 until the two orthogonal planes of the images formed by wedges 38 and 42 are angularly aligned with the two principal meridians of the cornea of eye 14. Then, wedge 38 is moved along optical axis 40 and wedge 42 is moved along optical axis 44 to align the images of the cross marks and dashes at eyepiece 13. The movement of wedges 38 and 42 to accomplish this alignment is measured, and the measurements indicate the corneal curvature.

When instrument 10 is used in the second operating mode, insertable wedge 46 and insertable mask 48 are merely inserted into system 30 and lamp 24 is activated. An image of the cornea is reflected from aligning axis 12 to system axis 32 by first reflecting system 50, through objective lens 34, mask 36, wedge 46, wedge 42 and mask 48, reflected from system axis 32 to aligning axis 12 by second reflecting system 52 and through eyepiece 13 to the eye of the user.

What is claimed is:

1. An ophthalmic instrument which utilizes a single imaging system for selectively measuring corneal curvature in the measuring mode of said instrument and for examining the surface of a cornea in the examining mode of said instrument, said instrument including a measuring light apparatus having an illuminated mire with apertures therethrough for projecting an image of said mire apertures through a cornea, said measuring light apparatus allowing the reflection of said mire image formed within the eye to pass through its center, said measuring light apparatus being disposed on an aligning axis about which said instrument may be rotated in order to align said instrument with the principal vertical and horizontal meridians of the eye in the measuring mode of said instrument, and a viewing light apparatus for projecting an image of the cornea along said aligning axis in the examining mode of said instrument, said instrument comprising:
    (a) reflecting means for displacing an image from said aligning axis to an imaging system axis and for returning said image to said aligning axis in an erect and unreversed position in order to provide both mire and corneal images in vertical and horizontal alignment with the cornea itself;
    (b) imaging system means disposed on said imaging system axis including objective lens means and optical wedge means for measuring the cornea in said measuring mode of said instrument and for examining the cornea in said examining mode of said instrument;
    (c) said optical wedge means including a first optical wedge having a first optical axis and a second optical wedge having a second optical axis; and
    (d) an eyepiece disposed on said aligning axis at the opposite end of said instrument from said measuring light apparatus for viewing said images.

2. The instrument of claim 1, wherein said imaging system means includes insertable masking means for permitting passage of light along only the second optical axis, said insertable masking means including a third optical wedge for focusing, in conjunction with said second optical wedge, said corneal image.

3. The instrument of claim 1, wherein said reflecting means includes a first series of mirrors for reflecting images from said aligning axis to said imaging system axis and a Porro mirror system for returning said images in an erect and unreversed position in order to provide both said mire and corneal images in vertical and horizontal alignment with the cornea itself.

* * * * *